(12) United States Patent
Giessler et al.

(10) Patent No.: US 6,225,507 B1
(45) Date of Patent: May 1, 2001

(54) METHOD OF PREPARING ALDEHYDES BY HYDROFORMYLATION WITH A RHODIUM CATALYST AND RECOVERY OF THE RHODIUM CATALYST BY EXTRACTION

(75) Inventors: Bernhard Giessler, Kirchheim; Heinz-Josef Kneuper, Mannheim; Michael Röper, Wachenheim; Rocco Paciello, Bad Dürkheim; Knut Oppenländer, Ludwigshafen; Wolfgang Günther, Mettenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/117,662

(22) PCT Filed: Feb. 12, 1997

(86) PCT No.: PCT/EP97/00635

§ 371 Date: Aug. 4, 1998

§ 102(e) Date: Aug. 4, 1998

(87) PCT Pub. No.: WO97/30016

PCT Pub. Date: Aug. 21, 1997

(30) Foreign Application Priority Data

Feb. 14, 1996 (DE) ................................. 19605435

(51) Int. Cl.[7] .................................. C07C 45/50
(52) U.S. Cl. ............................ 568/451; 568/909
(58) Field of Search .................... 568/451, 909

(56) References Cited

U.S. PATENT DOCUMENTS

| 4,400,547 |   | 8/1983 | Dawes et al. | 568/454 |
| 4,774,361 | * | 9/1988 | Maher et al. | 568/454 |
| 5,723,680 | * | 3/1998 | Kormann et al. | 568/455 |
| 5,919,987 | * | 7/1999 | Kneuper et al. | 568/451 |

FOREIGN PATENT DOCUMENTS

| 2604545 | 2/1976 | (DE) . |
| 82/03856 | 11/1982 | (DE) . |
| 3338340 | 10/1983 | (DE) . |
| 4230871 | 9/1992 | (DE) . |
| 695734 | 7/1995 | (EP) . |
| 1535603 | 1/1990 | (SU) . |
| 95/25080 | 9/1995 | (WO) . |

OTHER PUBLICATIONS

Falbe, *New Syntheses with Carbon Monoxide*, 1980, pp. 38–100.

Heil et al., *Chem Ber.*, vol. 102, pp. 2238–2240, 1969.

Fell et al., *Tetrahedron Letters*, No. 29, pp. 3261–3266, 1968.

Cornils et al., *Hydrocarbon Processing*, Jun. 1975, pp. 83–91.

* cited by examiner

Primary Examiner—Laura L. Stockton
(74) Attorney, Agent, or Firm—Keil & Weinkauf

(57) ABSTRACT

A process for the preparation of aldehydes or aldehydes and alcohols by hydroformylation of olefins containing more than 3 carbon atoms, comprising a hydroformylation stage, in which the olefin is hydroformylated under a pressure of form 50 to 1000 bar and at a temperature of from 50° to 180° C. by means of a rhodium catalyst dissolved in a homogenous reaction medium and a catalyst recovery stage comprising extraction of the rhodium catalyst with an aqueous solution of chelating agent, isolation of alcohols and/or aldehyde from the extracted hydroformylation product steam, precarbonylation of the aqueous rhodium-containing extract in the presence of carbon monoxide, synthesis gas as, or a gas mixture containing carbon monoxide under a pressure of from 50 to 1000 bar and at a temperature of from 50° to 180° C., separation of the effluent of the precarbonylation stage into an organic phase containing the major portion of the rhodium and an aqueous phase containing the chelating agent and recycling of the organic phase to the hydroformylation stage, where the rhodium catalyst is extracted from the effluent of the hydroformylation stage using an aqueous solution of a sulfonic acid group-free, water-soluble polymer capable of chelating rhodium.

15 Claims, 1 Drawing Sheet

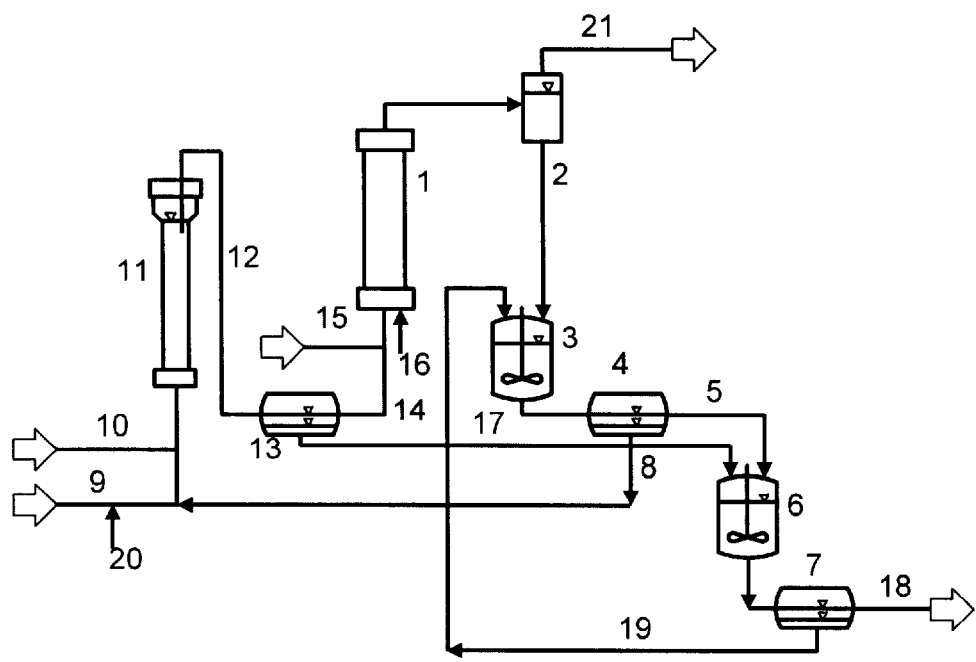

METHOD OF PREPARING ALDEHYDES BY HYDROFORMYLATION WITH A RHODIUM CATALYST AND RECOVERY OF THE RHODIUM CATALYST BY EXTRACTION

This application is a 371 of PCT/EP97/00635 filed Feb. 12, 1997.

DESCRIPTION

The present invention relates to a process for the preparation of alcohols and/or aldehydes by the hydroformylation of olefins containing more than 3 carbon atoms, comprising the stage of hydroformylation using a rhodium catalyst homogeneously dissolved in the reaction medium, the separation of the rhodium catalyst from the effluent of the hydroformylation reaction by extraction with an aqueous solution of a water-soluble complexing polymer, isolation of the hydroformylation product from the organic phase, and precarbonylation of the aqueous extract containing the rhodium with the addition of an essentially water-immiscible organic liquid and recycling of the organic phase to the hydroformylation.

The hydroformylation of olefins with carbon monoxide and hydrogen in the presence of transition metal catalysts is well known. While α-olefins are capable of hydroformylation to a high degree using rhodium-containing catalysts (cf J. Falbe, Ed.: New Syntheses With Carbon Monoxide, Springer, Berlin 1980, pp. 55 et seq), this catalyst system is less suitable for internal and internal, branched-chain olefins and also for olefins containing more than 7 carbon atoms (cf Falbe, pp. 95 et seq). Thus internal carbon—carbon double bonds are hydroformylated in the presence of such a catalyst only very slowly. Since the separation of the hydroformylation product from the homogeneous catalyst dissolved in the reaction system usually takes place by distillation and the boiling point of the aldehyde formed during hydroformylation increases with increasing carbon number and chain length to temperatures at which the rhodium-containing catalyst decomposes, this hydroformylation method is uneconomical for the hydroformylation of olefins containing more than 7 carbon atoms. In the hydroformylation of polymeric olefins such as polyisobutene, the noble metal-containing catalyst can not be recovered in a reusable form.

On the other hand internal and internal, branched-chain olefins can be advantageously hydroformylated with so-called "bare" rhodium, ie with homogeneous rhodium compounds dissolved in the hydroformylation medium and not modified with phosphorous ligands such as phosphines or phosphites. Such rhodium catalysts not modified with phosphines or phosphites and their suitability as catalysts for the hydroformylation of the aforementioned classes of olefins are known (cf Falbe, pp. 38 et seq). The terms "bare rhodium" or "bare rhodium catalysts" are used in this application for rhodium hydroformylation catalysts which are not modified, under the conditions of the hydroformylation, with ligands and particularly not with phosphorous ligands such as phosphine or phosphite ligands, unlike conventional rhodium hydroformylation catalysts. Carbonyl or hydrido ligands are not to be regarded as ligands in this context. It is assumed in the technical literature (cf Falbe, pp. 38 et seq), that the rhodium compound $HRh(CO)_4$ is the catalytically active rhodium species in the hydroformylation using "bare rhodium catalysts", although this is not absolutely proven on account of the many chemisms concurrently taking place in the hydroformylation reaction zone. Only for the sake of simplicity do we also go by this assumption in the present application, without this imposing any restriction on the scope of the invention, if at some time in the future a rhodium species other than that stated should turn out to be the actual catalytically active species. The "bare rhodium catalysts" form under the conditions of the hydroformylation reaction from rhodium compounds, eg rhodium salts, such as rhodium(III) chloride, rhodium(III) nitrate, rhodium(III) acetate, rhodium(II) acetate, rhodium(III) sulfate, or rhodium(III) ammonium chloride, from rhodium chalkogenides, such as rhodium(III) oxide or rhodium(III) sulfide, from salts of rhodium oxyacids, for example the rhodates, from rhodium carbonyl compounds, such as $Rh_4(CO)_{12}$ and $Rh_6(CO)_{16}$ or from organorhodium compounds, such as rhodium dicarbonyl acetylacetonate, cyclooctadiene rhodium acetate or chloride in the presence of $CO/H_2$ mixtures, generally designated as synthesis gas. For information on the execution of hydroformylations with "bare" rhodium reference may be made, at this juncture, to the following literature by way of example: U.S. Pat. No. 4,400,547; DE-A 3338340; DE-A 2604545; WO 82/03856; Chem. Ber. 102, 2238 (1969); Tetrahedron Lett. 29, 3261 (1968); Hydrocarbon Process. 85–86(1975).

However hydroformylation using "bare" rhodium also suffers from the drawback that the thermolabile rhodium catalyst (cf U.S. Pat. No. 4,400,547) partially decomposes to metallic rhodium on account of the thermal load imposed during purification, by distillation, of the hydroformylation product, which is deposited on the walls of the reactor and pipes. The precipitated metallic rhodium cannot be recycled to the hydroformylation reaction, since it cannot be converted back to the catalytically active rhodium compound under the hydroformylation conditions. The loss of rhodium caused by this chemical behavior of "bare rhodium catalysts" have hitherto prevented any large-scale use of this process.

Numerous processes have been proposed in the literature to solve these problems, of which the process described in DE-A 4,230,871 (further prior literature also cited in said reference) is a useful solution in the form of the extraction of the catalyst using sulfonated, nitrogenous, low molecular weight chelating agents and recycling of the extracted catalyst. This process has been further improved in the process described in WO 95/25080. Said reference describes an additional precarbonylation of the extract prior to recycling to the hydroformylation.

A process similar to that disclosed in WO 95/250080 is described in EP-A 695,734, in which the catalyst is extracted from the hydroformylation effluent by means of an aqueous solution of a phosphorous chelating agent selected from the group consisting of monosulfonated or polysulfonated and/or carboxylated monophosphanes or oligophosphanes. All of the phosphorous chelating agents disclosed in EP-A 695,734 are low molecular weight compounds.

Whilst this improvement of the process in its industrial form has made it possible to operate it on an industrial scale, the success of the extraction itself has remained unsatisfactory: on the one hand the degree of extraction and also the reversibility of complex formation and dissociation in the precarbonylation has been unsatisfactory and on the other hand the sulfonic acid group-containing low molecular-weight chelating agents described in the above two specifications are not readily available and are expensive, so that the object of the invention is to find extracting agents which are readily available are water-soluble without migrating into the organic phase to any substantial extent, and have strong complex-binding properties, so that good extracting efficiency is guaranteed.

According to the invention, this object has been achieved by means of a process for the preparation of aldehydes or aldehydes and alcohols by hydroformylation of olefins containing more than 3 carbon atoms, comprising a hydroformylation stage, in which the olefin is hydroformylated under a pressure of from 50 to 1000 bar and at a temperature of from 50° to 180° C. by means of a rhodium catalyst dissolved in a homogeneous reaction medium and a catalyst recovery stage comprising extraction of the rhodium catalyst with an aqueous solution of a chelating agent, isolation of alcohol and/or aldehyde from the extracted hydroformylation product stream, precarbonylation of the aqueous rhodium-containing extract in the presence of carbon monoxide, synthesis gas, or a gas mixture containing carbon monoxide under a pressure of from 50 to 1000 bar and at a temperature of from 50° to 180° C., separation of the effluent of the precarbonylation stage into an organic phase containing the major portion of the rhodium and an aqueous phase amended sheet containing the chelating agent and recycling of the organic phase to the hydroformylation stage, in which process the rhodium catalyst is extracted from the effluent of the hydroformylation stage using an aqueous solution of a sulfonic acid group-free, water-soluble, polymer which forms a water-soluble complex with the rhodium catalyst, and the rhodium is released, in the form of a lipophilic rhodium carbonyl compound, from the water-soluble complex formed, in the precarbonylation stage. The said water-soluble polymers are, in particular, selected from the group consisting of (a) poly(acrylic acid)s, which may be partially or completely neutralized and have an average molar mass of more than 500 g/mol
(b) maleic acid copolymers having an average molar mass of more than 3000 g/mol,
(c) mono- or poly-phosphonomethylated poly(vinyl amine)s having an average molar mass of more than 800 g/mol,
(d) mono- or poly-phosphonomethylated polyethyleneimines having an average molar mass of more than 200 g/mol, and/or
(e) mono- or poly-phosphonomethylated polyacrylamides having an average molar mass of more than 800 g/mol.

Suitable chelating agents forming water-soluble complexes with the rhodium catalyst dissolved in the effluent of the hydroformylation reaction are preferably nitrogenous phosphonomethylated chelating agents.

Suitable water-soluble, phosphonomethylated polymer to be used in the invention, are in particular phosphonomethylated polyamines substantially containing or consisting of units of the general formula 1

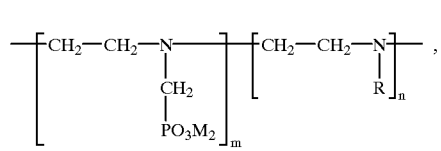

(1)

in which each M independently stands for hydrogen, ammonium, for a cation of a monovalent metal ion or for the equivalent of a polyvalent metal, in particular a metal selected from the group consisting of sodium, potassium, calcium, and magnesium, the average molecular weight of the water-soluble polymer being amended sheet from 200 to 2,000,000 g/mol, and the ratio of m to (n+m) is from 0.01:1 to 1:1, preferably from 0.5:1 to 1:1, and each radical R independently stands for hydrogen, alkyl, aryl, hydroxyalkyl, carboxyalkyl, and also, in particular, water-soluble, phosphonomethylated poly(vinyl amine)s substantially containing or consisting of units of the general formula 2

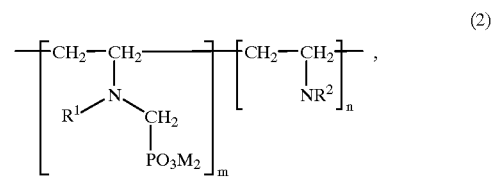

(2)

in which each M independently stands for hydrogen, ammonium, a cation of a monovalent metal or for the equivalent of a polyvalent metal, in particular a metal selected from the group consisting of sodium, potassium, calcium, and magnesium, where the average molecular weight of the water-soluble polymer is from 800 to 5,000,000g/mol and the ratio of m to (n+m) is from 0.01:1 to 1:1, preferably from 0.5:1 to 1:1, $R^1$ stands for R or $CH_2PO_3M_2$ and each R can independently be hydrogen, alkyl, aryl, hydroxyalkyl, or carboxyalkyl, and also, in particular, water-soluble, phosphonomethylated polyacrylamides substantially containing or consisting of units of the general formula 3

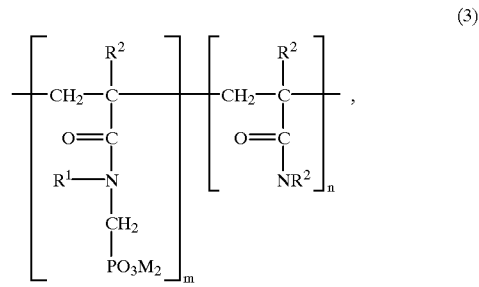

(3)

in which each M independently stands for hydrogen, for ammonium, for a cation of a monovalent metal or for the equivalent of a polyvalent metal, in particular a metal selected from the group consisting of sodium, potassium, calcium, and magnesium, where the average molecular weight of the water-soluble polymer is 800 to 5,000,000 g/mol and the ratio of m to (n+m) is 0.01:1 to 1:1, preferably 0.5:1 to 1:1, $R^1$ stands for R or $CH_2PO_3M_2$, $R^2$ for hydrogen or alkyl and where each R can independently be hydrogen, alkyl, aryl, hydroxyalkyl, or carboxyalkyl.

*J. Org. Chem.,* Vol. 31, 1603–1607 (1966) reveals the phosphonomethylation of amines. It operates on the analogy of the Mannich reaction, by causing amines exhibiting at least one NH group to react in the acid pH range with phosphorous acid and formaldehyde.

*Makromol. Chem.,* Vol. 128, 229 (1969) reveals that polymers (polyethyleneimine) can also be phosphonomethylated with formaldehyde and phosphorous acid in which polymers methyl phosphorous acid groups are attached to the polymeric framework.

It has been found that it is advantageous for the process of the invention when the degree of phosphonomethylation of the nitrogenous polymer (ratio of m to (m+n)) is as high as possible, since with increase in the degree of phosphonomethylation the water solubility of the extracting agent increases and the separation of the organic and aqueous phases following precarbonylation is improved.

Other suitable water-soluble polymers for the process of the invention are poly(acrylic acid)s or partially or completely neutralized poly(acrylic acid)s substantially containing or consisting of units of the general formula 4

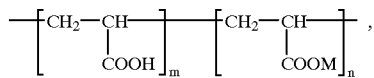
(4)

where M stands for ammonium, for a cation of a monovalent metal or for the equivalent of a polyvalent metal and the average molar mass of the water-soluble polymer is from 500 to 250,000 g/mol and the ratio of m to (n+m) is from 0.01:1 to 1:1, preferably from 0.2:1 to 0.7:1, and also water-soluble poly(acrylic acid-co-maleic acid)s or partially or completely neutralized poly(acrylic acid-co-maleic acid) preferably those containing or consisting of units of the general formula 5

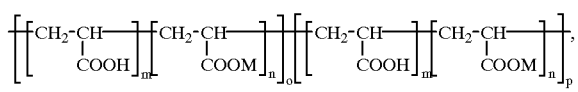
(5)

where M stands for ammonium, for a cation of a polyvalent metal or for the equivalent of an polyvalent metal and the average molar mass of the water-soluble polymer is from 3000 to 70,000 g/mol and the ratio of m to (n+m) is from 0.01:1 to 1:1, preferably from 0.2:1 to 0.7:1 and the ratio of o to (o+p) is from 0:1 to 1:1, preferably from 0.3:1 to 0.7:1.

The excellent suitability of the aqueous solutions of the water-soluble polymers of said type was surprising, since both the resistance to the high pressures and temperatures prevailing in the carbonylation and the non-transfer to the organic phase was not to have been expected.

Specifically, according to the invention, the rhodium-containing hydroformylation effluents obtained during hydroformylation with "bare rhodium" are admixed with water-soluble polymer capable of forming complexes with the rhodium catalyst which are hydrophilic and can be extracted from the organic medium of the hydroformylation product stream with water. Following separation, by extraction, of the rhodium catalyst present in the hydroformylation effluent in the form of a water-soluble complex with the water-soluble polymer used in the process of the invention, the hydroformylation product can be purified in a manner known per se, for example by removing the hydroformylation product from the organic extract, by distillation, or by removing, by distillation, the more readily volatile organic components of the hydrodormylation effluent from the less readily volatile or even non-volatile hydroformylation product. The aqueous extract of the hydroformylation product stream, which contains the rhodium catalyst now complexed by the water-soluble polymer, is passed to a precarbonylation stage, as described in WO 95/25080, in which the chelated rhodium catalyst is subjected to carbonylation in the presence of a substantially water-insoluble, organic liquid and in the presence of carbon monoxide, synthesis gas, or a gas mixture containing carbon monoxide under a pressure of generally from 50 to 1000 bar, preferably from 70 to 500 bar and more preferably from 100 to 400 bar and at a temperature of from 500 to 180° C., preferably from 70° to 160° C. and more preferably from 90° to 140° C. This carbonylation causes the rhodium to be dissolved out of the hydrophilic complex with the water-soluble polymer, and the lipophilic rhodium carbonyl compound migrates as "bare" rhodium into the water-insoluble, organic liquid. This step is designated as "precarbonylation", since the carbonylation of the rhodium does not take place in the hydroformylation reactor itself, but in the upstream precarbonylation stage.

The effluent from the precarbonylation stage can be readily separated into an organic phase containing the major portion of rhodium in the form of a rhodium carbonyl compound and an aqueous phase containing the major portion of the water-soluble polymer, eg in a phase separator. The organic phase is afterwards transferred to the hydroformylation stage, in which the "bare" rhodium present in this catalyst solution catalyzes the hydroformylation of olefin to be hydroformylated. The aqueous phase containing the major portion of the water-soluble polymer can be used for some other purpose, for example advantageously for the extraction of the rhodium catalyst from the hydroformylation product stream.

The precarbonylation can be carried out using carbon monoxide, synthesis gas, or a gas mixture containing carbon monoxide. By synthesis gas we mean $CO/H_2$ gas mixtures in which carbon monoxide and hydrogen are present generally in a molar ratio of from 1:5 to 5:1 and preferably from 4:6 to 6:4. The expression "gas mixtures containing carbon monoxide" should be taken to mean, for the purposes of this application, other gas mixtures containing carbon monoxide which do not come under the heading of "synthesis gas", for example $CO/H_2$ mixtures of a composition other than that of synthesis gas or mixtures of carbon monoxide with other gases inert under the reaction conditions, such as nitrogen, noble gases, or lower hydrocarbons such as methane, ethane, propane, or butane.

According to the invention, the substantially water-insoluble organic liquid that can be used may be one of a large number of liquids inert under the reaction conditions of the precarbonylation and hydroformylation stages, where "inert" means that these liquids do not have an adverse effect on the operation of the precarbonylation or hydroformylation.

Examples of such organic liquids that can be used are hydrocarbons. However aldehydes or alcohols or mixtures of aldehydes and alcohols are preferably used. For example a portion of the crude effluent from the hydroformylation stage can be used for this purpose or, alternatively, the organic aldehydes or alcohols formed in the hydroformylation stage and subsequently isolated therefrom or mixtures thereof can be used. There are generally virtually no restrictions as regards the type of crude aldehydes used as water-insoluble, organic liquid in the precarbonylation stage. However those aldehydes or alcohols are preferably used as are formed in the hydroformylation of the organic olefin to be hydroformylated.

The substantially water-insoluble, organic liquid that can be used in the precarbonylation stage can also be a so-called high boiler. These are high-boiling condensation products of aldehydes, which are formed during hydroformylation as by-products. Of course these are generally multi-component mixtures. U.S. Pat. No. 4,148,830 explains the chemical nature of such high boiler mixtures by way of example. Such high boiler mixtures are also commercially available; for example as sold by Eastman under the Registered Trade Name Texanol®. More preferably, olefins are used as substantially water-insoluble, organic liquids in the precarbonylation stage. Although basically no restriction holds regarding the type of olefin used in the precarbonylation, those olefins are preferably used which are employed in the following hydroformylation stage of the starting olefins.

It may also be found to be advantageous to feed the entire olefin input stream for the hydroformylation stage first of all through the precarbonylation stage. If synthesis gas is used in the precarbonylation stage as carbonylation gas, the olefin fed in can already be hydroformylated in small amounts depending on the conditions used in the precarbonylation. If carbon monoxide or a gas mixture containing carbon monoxide is used as carbonylizing agent, acyl complexes of the carbonylated rhodium can form with the olefin, by which means additional stabilization of the homogeneously dissolved rhodium can be achieved.

Since the isomerization of α-olefins to internal α-olefins can take place when use is made of olefins in ax precarbonylation stage, α-olefins can be isomerized to internal olefins and these can be hydroformylated to internal, ie branched-chain aldehydes in the following hydroformylation stage. This is particularly advantageous, since α-olefins, compared with internal olefins, are commercially available in larger quantities than internal olefins, whilst α-olefins can be obtained more cheaply than internal olefins and branched-chain aldehydes and branched-chain alcohols are desirable intermediates for the preparation of branched-chain carboxylic acids, alcohols, and amines, which are in turn extensively used, eg, as additives for detergents and cleaners and for the preparation of biologically degradable surfactants.

For the preparation of branched-chain alcohols and/or aldehydes from α-olefins the α-olefin feed is conveniently passed through the precarbonylation stage. The precarbonylation and, simultaneously therewith, the isomerization of α-olefin to the internal olefin is generally carried out at temperatures ranging from 100° to 180° C., preferably from 120° to 160° C. and more preferably from 130° to 150° C. and under a pressure of from 50 to 1000 bar, preferably from 70 to 500 bar and more preferably from 100 to 400 bar. The residence time required to achieve complete isomerization of the α-olefin in the precarbonylation stage is generally governed by the reaction conditions used therein and is conveniently determined by a preliminary test.

Of course the present process can also be used to hydroformylate α-olefins to n-aldehydes for example by passing the α-olefin into the hydroformylation reactor whilst by-passing the precarbonylation stage or by using reaction conditions in the precarbonylation stage such that the α-olefin fed therethrough is not isomerized to any appreciable extent.

The precarbonylation stage can consist of one or more parallel or in-line reactors. When using a batchwise mode of operation it is possible to employ conventional stirred autoclaves for this purpose and for a continuous mode of operation cascaded stirred autoclaves or tubular reactors containing means for thorough mixing of the reaction mixture can be used.

The effluent from the precarbonylation stage is separated into an aqueous and an organic phase in suitable equipment, eg a phase separator. The phase separation can take place under pressure, for example the operating pressure of the precarbonylation stage or under atmospheric pressure, following previous depressurization of the effluent from the precarbonylation. Since both the precarbonylation and the hydroformylation take place under elevated pressure, the phase separation is advantageously likewise carried out under pressure.

The organic phase thus separated from the effluent of the precarbonylation stage, which contains the bare rhodium required for catalysis of the hydroformylation and, depending on the type of water-insoluble, organic liquid used in the precarbonylation stage, the olefin to be hydroformylated or some other suitable organic liquid, can be fed to the hydroformylation stage. If no depressurization and degasification of the precarbonylation effluent is carried out, the organic phase still contains the gaseous carbonylizing agent used in the precarbonylation stage, substantially in dissolved form.

The hydroformylation is carried out in the presence of synthesis gas using the bare rhodium catalyst produced in the precarbonylation stage. If necessary the olefin to be hydroformylated is fed to the hydroformylation stage, if this has not already been done together with the organic phase from the precarbonylation effluent.

The hydroformylation is generally carried out at temperatures ranging from 60° to 180° C., preferably from 80° to 140° C. and more preferably from 90° to 130° C. and under a pressure generally of from 50 to 1000 bar, preferably from 70 to 500 bar and in particular from 100 to 400 bar. The hydroformylation otherwise takes place under conditions such as are usually employed in hydroformylations using bare rhodium and as described for example in the literature cited above with respect to hydroformylation using bare rhodium.

The ratio of the products alcohol:aldehyde in the hydroformylation product stream can be influenced by the conditions of pressure and temperature used in the hydroformylation stage and the synthesis gas composition. For example, for given synthesis gas compositions—molar ratio of $CO:H_S$ 50:50, 40:60 and 60:40 respectively—, the hydroformylation of trimerpropylene—carried out at a temperature of 130° C. and under a pressure of 280 bar—a molar ratio of aldehyde to alcohol of 93:7 is attained in each case. When the temperature is increased from 130° C. to 150° C. the molar ratio of aldehyde to alcohol in the hydroformylation product stream changes as a function of the synthesis gas composition—$CO:H_2$ molar ratio 50:50, 40:60, and 60:40— to 76:24, 67:33, and 82:18 respectively.

The hydroformylation can be carried out in the presence or absence of organic solvents. The use of organic solvent is particularly advantageous, especially in the hydroformylation of long-chain or polymeric olefins. The solvents used can be those usually employed in hydroformylation processes, for example high-boiling aldehyde condensation products formed during the hydroformylation reaction as by-products resulting from the condensation of the aldehydes produced.

The effluent from the hydroformylation stage is conveniently depressurized prior to its extraction with the aqueous solution of the nitrogenous chelating agent. The extraction of the hydroformylation product stream is generally carried out at temperatures ranging from 50° to 140° C., preferably from 70° to 130° C. and more preferably from 90° to 120° C. and under a pressure of generally from 1 to 20 bar, preferably from 1 to 10 bar and more preferably from 1 to 5 bar. The extraction can be carried out in air or under an inert gas atmosphere, for example an atmosphere of nitrogen, hydrogen, or argon. However, it may be advantageous to add carbon monoxide or synthesis gas to the inert gas used or to carry out the extraction in the presence of carbon monoxide.

To extract the rhodium catalyst from the hydroformylation product stream use can be made of a fresh aqueous solution of the chelating agent, but this is preferably achieved by using the aqueous phase obtained in the phase separation of the precarbonylation effluent and containing the dissolved chelating agent, which aqueous phase is recycled to the extraction stage for this purpose.

During extraction the ratio by volume of aqueous to organic phase is generally adjusted to from 0.2:1 to 2:1 and preferably from 0.3:1 to 1:1. The content of water-soluble, polymeric extracting agents in the aqueous phase is generally from 0.1 to 50%, preferably from 1 to 30% and more preferably from 3 to 10%.

Suitable apparatus for the extraction of the hydroformylation product stream with the aqueous solution of the water-soluble polymer are practically all liquid—liquid extractors, for example mixer-settlers, bubble-cap columns, or counter-flow or parallel-flow extracting columns, where these can be equipped with additional internal fittings to improve the efficiency of mixing of the aqueous and organic phases, for example sieve trays, filling material, or static mixers. The extraction of the rhodium catalyst from the hydroformylation product stream can be carried out in a single srage, but preferably a multistage extraction is used, for example a two-stage or three-stage extraction, in which the aqueous phase containing the chelating agent phase is caused to flow parallel to or, more preferably, countercurrently to the organic phase.

On completion of the extraction the hydroformylation product stream freed from rhodium catalyst can be purified in conventional manner, for example by distillation in order to isolate the desired alcohols and/or aldehydes present therein.

BRIEF DESCRIPTION OF DRAWING

One advantageous embodiment of the process of the invention is illustrated diagrammatically in FIG. 1 and explained below. Obvious details of the plant, which are not necessary for the illustration of the process of the invention, are not shown in FIG. 1 for the sake of clarity. The embodiment shown in FIG. 1 of the process of the invention embraces the process stages of hydroformylation, a two-stage counter-flow extraction of the hydroformylation product stream using mixer/settler equipment and the precarbonylation stage. It is obvious that other extraction equipment mentioned above can be used instead of the mixer/settler equipment, if desired.

In the embodiment of the process of the invention illustrated in FIG. 1, the hydroformylation product stream coming from the hydroformylation reactor 1 via pipe line 2 after depressurization, separation of the liquid phase from excess synthesis gas (exhaust gas) via pipe line 21 and optionally following the feed of inert gas (not shown), is fed to the extracting stage A, comprising the mixer/settler 3/4, where it is extracted with the aqueous solution of the water-soluble polymer coming from extracting stage C (mixer/settler 6/7) fed in via pipe line 19. At the commencement of the process or for the purpose of replenishing the aqueous polymer solution, fresh polymer solution can be fed to, say, the mixer 3 via an inlet not shown in FIG. 1. The extraction mixture present in the mixer 3 is separated in the settler 4 into a first organic and a first aqueous phase. The first aqueous phase is passed, via pipe line 8, to the precarbonylation reactor 11, whereas the first organic phase is fed, via pipe line 5, to the extraction 6 (extracting stage C). Prior to introduction into the precarbonylation reactor 11 the first aqueous phase is further mixed, in suitable mixing equipment, via inlets 9 and 10, with a substantially water-insoluble, organic liquid, for example crude hydroformylation product stream, Texanol® or preferably the olefin to be hydroformylated and the carbonylizing agent, ie carbon monoxide, synthesis gas, or a suitable gas mixture containing carbon monoxide, preferably with carbon monoxide or synthesis gas. It is theoretically also possible to introduce the starting materials flowing through the pipe lines 9 and 10 directly into the precarbonylation reactor 11. In the precarbonylation reactor 11 the rhodium attached to the water-soluble polymer and present in the aqueous phase is subjected to carbonylation under the conditions stated and the resulting, lipophilic bare rhodium catalyst migrates into the organic phase. The effluent from the precarbonylation reactor 11 is passed to the phase separator 13 via pipe line 12, preferably without previous depressurization, where it is separated into a second organic and a second aqueous phase (phase separating stage B).

The second organic phase, which contains, in addition to the water-insoluble, organic liquid, the dissolved components bare rhodium as required for the catalysis of the hydroformylation and, optionally, excess carbonylizing agent, is passed via pipe line 14 into the hydroformylation reactor 1. Synthesis gas is fed through pipe line 15 to the hydroformylation reactor, but this can alternatively be fed to the hydroformylation reactor 1. If no olefin is used in the precarbonylation reactor as the water-insoluble, organic liquid, the olefin to be hydroformylated can be either directly fed through pipe line 16 into the hydroformylation reactor 1 or previously mixed with the stream in line 14 via an inlet not shown in FIG. 1. In the hydroformylation reactor the olefin is hydroformylated to the corresponding alcohols and/or aldehydes under the stated conditions.

The second aqueous phase from the phase separation 13 (phase separating stage B), which contains the rhodium-depleted solution of the water-soluble polymer, is fed in via pipe line 17 to the mixer 6 following previous depressurization. In extracting stage C, comprising the mixer 6 and the settler 7, the first organic phase from extracting stage A is again extracted with the second aqueous phase from phase separating stage B in order to remove residual amounts of rhodium from the first organic phase. The extraction mixture present in the mixer 6 is separated in the settler 7 into a third organic and a third aqueous phase. The third organic phase, now free from rhodium, is discharged through pipe line 18 for the purpose of further purification to isolate the desired products—alcohol and/or aldehyde. The third aqueous phase from extracting stage C is passed through pipe line 19 to the extracting stage A, which closes the circuit.

The reactor can be charged with rhodium for the first time by the introduction of a solution or suspension of the rhodium catalyst or precursors as mentioned above which are suitable for the preparation of the rhodium catalyst, into, say, the precarbonylation reactor 11 or the hydroformylation reactor 1. The same applies when it is necessary to replenish spent catalyst. It is also possible to introduce the rhodium into the plant via pipe line 20 or other inlets not shown in the drawing, for example via an inlet in pipe line 8.

The process of the invention is particularly well suited for the hydroformylation of olefins containing more than 3 and preferably more than 7 carbon atoms, in particular for the hydroformylation of $C_7$–$C_{20}$ olefins, which can be straight-chain or branched-chain and which can contain α-olefinic and/or internal double bonds, eg octene-1, dodecene-1, trimer- and tetramer-propylene, or dimer- trimer- and tetramer-butylene. Similarly, unsaturated oligomers of other oletins can be hydroformylated. Likewise different co-oligomers of other olefins. The aldehydes formed from these olefins serve, eg, as intermediates for the preparation of plasticizer alcohols and surfactants, which can be produced therefrom in conventional manner by hydrogenation. The olefins used for the hydroformylation can be obtained eg by the acid-catalyzed elimination of water from the corresponding fatty alcohols or according to a large number of other technical processes as are described, for example, in Weissermel, Arpe: Industrielle Organische Chemie, pp 67–86, Verlag Chemie, Weinheim, 1978. If α-olefins are used in the process of the invention these can be either hydroformylated to the corresponding n-aldehydes by direct feed into the hydroformylation stage or hydroformylated to isoaldehydes by their feed to the precarbonylation stage, following their isomerization to form internal olefins, to the use of which reference is made above.

The process of the invention is also particularly well suited for the hydroformylation of polymeric olefins, for example low molecular-weight polyisobutene, low molecular-weight polybutadiene or low molecular-weight poly(1,3-butadiene-co-isobutene) or poly(1,3-butadiene-co-butene). By low molecular-weight polymers we mean in particular polymers having molecular weights of from 280 to 5000° alton. It is also possible, however, to hydroformylate unsaturated polymers of higher molecular weight, ie having molecular weights above 5000. The only prerequisite for this is that they must be soluble in the hydroformlyation medium.

The present process is thus suitable for the preparation of virtually all aldehydes which are obtainable via the hydroformylation of olefins. We would emphasize that for example substituted olefins, which can generally carry one or two but preferably one substituent, can also be hydroformylated by the process of the invention. For example unsaturated, aliphatic carboxylates, acetals, alcohols, ethers, aldehydes, ketones, amines and amides can be hydroformylated by the process of the invention. Such substituted starting olefins which are of interest are eg methacrylates, dicyclopentadiene, vinyl ether and allyl ether and in particular corresponding substituted derivatives of unsaturated fatty acids, for example the esters of oleic, linoleic, linolenic, ricinic, or erucic acid. The aldehydes which can be obtained from these olefinic raw materials by hydroformylation are likewise starting materials for the preparation of biologically readily degradable, surface-active substances.

Another possibility is provided by a process for the preparation of branched-chain carboxylic acids, alcohols or amines from α-olefins, the α-olefins being isomerized to internal olefins in the precarbonylation stage and then hydroformylated to isoaldehydes and the isoaldehydes thus obtained being oxidized to branched-chain carboxylic acids in conventional manner, reduced to branched-chain alcohols or reductively aminated to branched-chain amines by the present process. The oxidation of isoaldehydes or isoaldehyde/n-aldehyde mixtures obtained from α-olefins can take place in known manner, for example by the oxidation of aldehydes with atmospheric oxygen or with oxygen by the methods described in eg Ullmann's Encyclopedia of Industrial Chemistry, 5th Edition, Vol. A5, pp 239, VCH Verlagsgesellschaft, Weinheim, 1986.

The catalytic hydrogenation of isoaldehydes or isoaldehyde/n-aldehyde mixtures obtained in the process of the invention from α-olefins to produce branched-chain alcohols can be effected in known manner, for example by the processes described in Ullmann's Encyclopedia of Industrial Chemistry, 5th Edition., Vol. A1, pp 279, VCH Verlagsgesellschaft, Weinheim, 1985 or G. H. Ludwig, Hydrocarbon Processing, March 1993, pp 67.

The reductive amination of isoaldehydes or isoaldehyde/n-aldehyde mixtures obtained in the process of the invention from α-olefins can take place in known manner, for example by the processes described in Ullmann's Encyclopedia of Industrial Chemistry, 5th Edition, Vol. A2, pp 1, VCH Verlagsgesellschaft, Weinheim, 1985. The starting material for the preparation of amines that can be used comprises ammonia, primary $C_2$–$C_{20}$ amines or secondary $C_2$–$C_{20}$ amines.

EXAMPLE 1

(phosphonomethylated polyethyleneimine, average molar mass 6500 g/mol, ratio m:(n+m) =0.9:1)

Extraction: 125 mL of an effluent from the hydroformylation of octene-N (an isomer mixture of butene dimers) were extracted with 125 mL of an aqueous solution of phosphonomethylated polyethyleneimine. Of the 71 ppm of rhodium by weight originally present there were still 4ppm by weight in the organic phase following the extraction.

Precarbonylation: 75 mL of an aqueous, rhodium-containing solution to be extracted containing phosphonomethylated polyethyleneimine were stirred with 75 mL of octene-N in an autoclave under a carbon monoxide pressure of 280 bar and a temperature of 130° C. over a period of 3 hours. During this operation the rhodium attached to the water-soluble polymer was subjected to carbonylation and extracted into the aqueous phase. The organic phase contained 40 ppm by weight and the aqueous phase 9 ppm of rhodium by weight, whilst the water-soluble polymer remained in the aqueous phase.

Hydroformylation: the effluent from the precarbonylation reactor was separated into an aqueous and an organic phase. The organic phase was then hydroformylated at 130° C. and a synthesis gas pressure ($CO/H_2$ ratio 1:1) of 260 bar in a hydroformylation reactor. The conversion achieved in the hydroformylation was 93%.

EXAMPLE 2

(poly(acrylic acid) partially neutralized, average molar mass 1000 g/mol ratio m:(n+m) =0.5)

Extraction: 125 mL of an effluent from the hydroformylation of octene-N (an isomer mixture of butene dimers) were extracted with 125 mL of an aqueous solution of partially neutralized poly(acrylic acid). Of the 100ppm by weight of rhodium originally present there were still 6 ppm by weight in the organic phase following the extraction.

Precarbonylation: 75 mL of an aqueous, rhodium-containing solution to be extracted containing partially neutralized poly(acrylic acid) were stirred with 75 mL of octene-N in an autoclave under a carbon monoxide pressure of 280 bar and a temperature of 130° C. over a period of 3 hours. The rhodium attached to the water-soluble polymer was subjected to carbonylation and extracted into the organic phase. The organic phase contained 40 ppm by weight of rhodium and the aqueous phase 7 ppm, by weight, whilst the water-soluble polymer remained in the aqueous phase.

Hydroformylation: the effluent from the precarbonylation reactor was separated into an aqueous and an organic phase. The organic phase was then hydroformylated at 130° C. and a synthesis gas pressure ($CO/H_2$ ratio 1:1) of 280 bar in a hydroformylation reactor. The conversion achieved in the hydroformylation was 97.

EXAMPLE 3

As described with reference to FIG. 1, a continuous experiment was carried out using water-soluble phosphonomethylated polyethyleneimine, average molar mass 6500g/mol, ratio m:(n+m) =0.9:1.

feeds (per hour):
  10: 200 g isooctene
  9: 20 liters (STP) of CO
  8: 200 g of catalyst solution containing 20 ppm of rhodium
  15: 100 liters (STP) of synthesis gas
temperature:
  precarbonylation (11) 100° C.
  reactor (1) 120° C.
effluent (per hour):
  18: 228 g of effluent containing 0.4 ppm of rhodium

What is claimed is:

1. A process for the preparation of aldehydes or aldehydes and alcohols by hydroformylation of olefins containing more than 3 carbon atoms, comprising a hydroformylation stage, in which the olefin is hydroformylated under a pressure of from 50 to 1000 bar and at a temperature of from 50° to 180° by means of a rhodium catalyst dissolved in a homogenous reaction medium and a catalyst recovery stage comprising extraction of the rhodium catalyst with an aqueous solution of a chelating agent, isolation of alcohol and/or aldehyde from the extracted hydroformylation product stream, precarbonylation of the aqueous rhodium-containing extract in the presence of carbon monoxide, synthesis gas, or a gas mixture containing carbon monoxide under a pressure of from 50 to 1000 bar and at a temperature of from 50° to 180° C., separation of the effluent of the precarbonylation stage into an organic phase containing the major portion of the rhodium and an aqueous phase containing the chelating agent and recycling of the organic phase to the hydroformylation stage, wherein the rhodium catalyst is extracted from the effluent of the hydroformylation stage using an aqueous solution of a sulfonic acid group-free, water-soluble, polymer which forms a water-soluble complex with the rhodium catalyst, and the rhodium is released, in the form of a lipophilic rhodium carbonyl compound, from the water-soluble complex formed, in the precarbonylation stage.

2. A process for the preparation of aldehydes or aldehydes and alcohols by hydroformylation of olefins containing more than 3 carbon atoms as defined in claim 1, comprising a hydroformylation stage, in which the olefin is hydroformylated under a pressure of from 50 to 1000 bar and at a temperature of from 50° to 180° C. by means of a rhodium catalyst dissolved in a homogeneous reaction medium and a catalyst recovery stage comprising extraction of the rhodium catalyst with an aqueous solution of a chelating agent, isolation of alcohol and/or aldehyde from the extracted hydroformylation product stream, precarbonylation of the aqueous rhodium-containing extract in the presence of carbon monoxide, synthesis gas, or a gas mixture containing carbon monoxide under a pressure of from 50 to 1000 bar and at a temperature of from 50° to 180° C., separation of the effluent of the precarbonylation stage into an organic phase containing the major portion of the rhodium and an aqueous phase containing the chelating agent and recycling of the organic phase to the hydroformylation stage, wherein the rhodium catalyst is extracted from the effluent of the hydroformylation stage using an aqueous solution of a sulfonic acid group-free, water-soluble, polymer selected from the group consisting of (a) poly(acrylic acid)s, which may be partially or completely neutralized and have an average molar mass of more than 500 g/mol,
(b) maleic acid copolymers having an average molar mass of more than 3000 g/mol,
(c) mono- or poly-phosphonomethylated poly(vinyl amine)s having an average molar mass of more than 800 g/mol,
(d) mono- or poly-phosphonomethylated polyethyleneimines having an average molar mass of more than 200 g/mol, and
(e) mono- or poly-phosphonomethylated polyacrylamides having an average molar mass of more than 800 g/mol.

3. A process as defined in claim 1, wherein the water-soluble extracting agent used is a water-soluble salt of a phosphonomethylated polyethyleneimine substantially containing units of the general formula

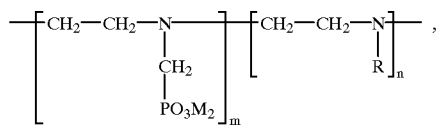

in which each M independently stands for hydrogen, ammonium, for a monovalent metal ion or for the equivalent of a polyvalent metal, where the average molecular weight of the water-soluble polymer is from 200 to 2,000,000 g/mol, and the ratio of m to (n+m) is from 0.01:1 to 1:1, and each radical R independently stands for hydrogen, alkyl, aryl, hydroxyalkyl, or carboxyalkyl.

4. A process as defined in claim 1, wherein the water-soluble extracting agent used is a water-soluble salt of a phosphonomethylated poly(vinyl amine) containing units of the general formula

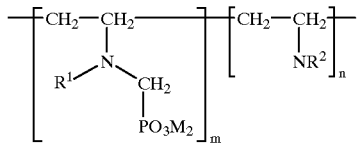

in which each M independently stands for hydrogen, ammonium, a cation of a monovalent metal or for the equivalent of a polyvalent metal where the average molecular weight of the water-soluble polymer is from 800 to 5,000,000 g/mol and the ratio of m to (n+m) is from 0.01:1 to 1:1, $R^1$ stands for R or $CH_2PO_3M_2$ and each R independently is hydrogen, alkyl, aryl, hydroxyalkyl, or carboxyalkyl.

5. A process as defined in claim 1, wherein the water-soluble extracting agent used is a water-soluble salt of a phosphonomethylated polyacrylamide containing units of the general formula (3)

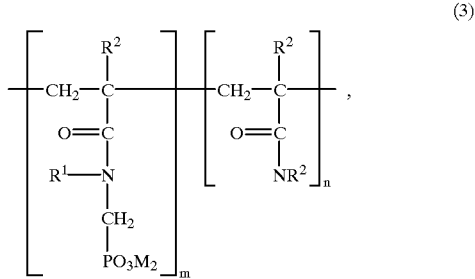

in which each M independently stands for hydrogen, for ammonium, for a cation of a monovalent metal or for the equivalent of a polyvalent metal, where the average molecular weight of the water-soluble polymer is 800 to 5,000,000 g/mol and the ratio of m to (n+m) is 0.01:1 to 1:1, $R^1$ stands for R or $CH_2PO_3M_2$, $R^2$ for hydrogen or alkyl and where each R independently is hydrogen, alkyl, aryl, hydroxyalkyl, or carboxyalkyl.

6. A process as defined in claim 1, wherein the water-soluble extracting agent used is poly(acrylic acid) or a partially or completely neutralized salt of a poly(acrylic acid) containing units of the general formula

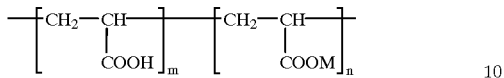

where M stands for ammonium, for a cation of a monovalent metal or for the equivalent of a polyvalent metal and the average molar mass of the water-soluble polymer is from 500 to 250,000a/mol and the ratio of m to (n+m) is from 0.01:1 to 1:1.

7. A process as defined in claim 1, wherein the water-soluble extracting agent used is a poly(acrylic acid-co-maleic acid) or a partially or completely neutralized salt of a poly(acrylic acid-co-maleic acid) containing units of the general formula

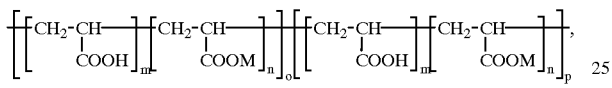

where M stands for ammonium, for a cation of a polyvalent metal or for the equivalent of a polyvalent metal and the average molar mass of the water-soluble polymer is from 3000 to 70,000 g/mol and the ratio of m to (m+n) is from 0.01:1 to 1:1, and the ratio of o to (o+p) is from 0.01:1 to 1:1.

8. A process as defined in claim 1, wherein essentially water-insoluble organic liquid crude effluent from the hydroformylation stage is used in the precarbonylation stage.

9. A process as defined in claim 1, wherein essentially water-insoluble organic liquid α-olefin to be hydroformylated is used in the precarbonylation stage, and the precarbonylation is carried out under a pressure of more than 100 bar and a temperature of less than 110° C.

10. A process as defined in claim 1, wherein the process is continuous and the effluent from the hydroformylation stage is extracted in an extracting stage A with the aqueous solution of the polymeric extracting agent coming from a second extracting stage C, the said extraction mixture of extracting stage A is separated into a first aqueous phase and a first organic phase, the first aqueous phase is fed to the precarbonylation stage and the first organic phase to the extracting stage C, the complexed rhodium present in the first aqueous phase is carbonylated in the precarbonylation stage in the presence of a substantially water-insoluble organic liquid using carbon monoxide, synthesis gas, or a gas mixture containing carbon monoxide, the effluent from the precarbonylation stage is separated in a phase separator B into a second organic phase and a second aqueous phase, the second organic phase is fed to the hydroformylation reactor and the second aqueous phase to the extracting stage C, the olefin is hydroformylated in the hydroformylation stage in the presence of synthesis gas, the second aqueous phase is used for extraction of residual catalyst from the first organic phase in extracting stage C, the extraction mixture from extraction stage C is separated into a third organic phase and a third queous phase, the aldehyde and/or alcohol is isolated from the third organic phase, and the third aqueous phase is recycled to the extracting stage A for the purpose of extracting the rhodium catalyst from the hydroformylation effluent.

11. A process as defined in claim 3, wherein the ratio of m to (n+m) is from 0.5:1 to 1:1.

12. A process as defined in claim 4, wherein the ratio of m to (n+m) is from 0.5:1 to 1:1.

13. A process as defined in claim 5, wherein the ratio of m to (n+m) is from 0.5:1 to 1:1.

14. A process as defined in claim 6, wherein the ratio of m to (n+m) is from 0.2:1 to 0.7:1.

15. A process as defined in claim 7, wherein the ratio of m to (m+n) is from 0.2:1 to 0.7:1 and the ratio of o to (o+p) is from 0.3:1 to 0.7:1.

* * * * *

UNITED STATES PATENT AND TRADEMARK OFFICE
CERTIFICATE OF CORRECTION

PATENT NO. : 6,225,507 B1 Page 1 of 1
DATED : May 1, 2001
INVENTOR(S) : Geissler et al.

It is certified that error appears in the above-identified patent and that said Letters Patent is hereby corrected as shown below:

ABSTRACT,
Line 5, "from" should be -- form --.

Column 16, claim 10,
Line 25, "queous" should be -- aqueous --.

Signed and Sealed this

Twenty-fifth Day of December, 2001

Attest:

JAMES E. ROGAN
*Attesting Officer*     *Director of the United States Patent and Trademark Office*